(12) United States Patent
Giesinger et al.

(10) Patent No.: US 6,355,801 B1
(45) Date of Patent: Mar. 12, 2002

(54) PROCESS FOR PREPARING N-(4-HYDROXYPHENYL)-N'-(4'-AMINOPHENYL)-PIPERAZINE

(75) Inventors: Brigitte Giesinger, Basel; Ingrid Mergelsberg, Dagmersellen, both of (CH)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 09/707,018

(22) Filed: Nov. 6, 2000

Related U.S. Application Data
(60) Provisional application No. 60/164,296, filed on Nov. 8, 1999.

(51) Int. Cl.$^7$ ............................................. C07D 295/033
(52) U.S. Cl. ...................................................... 544/392
(58) Field of Search ......................................... 544/392

(56) References Cited

U.S. PATENT DOCUMENTS

| | | | |
|---|---|---|---|
| 4,931,444 A | * 6/1990 | Van Wauwe et al. | 514/252 |
| 5,688,795 A | * 11/1997 | Pfister et al. | 514/252 |
| 5,710,155 A | 1/1998 | Schnorrenberg et al. | 514/255 |
| 5,780,475 A | 7/1998 | Baker et al. | 514/255 |

FOREIGN PATENT DOCUMENTS

EP   0 331 232   2/1989

OTHER PUBLICATIONS

Hepperle et al Tetrahedron Letters 40 (1999) 5655—5659.*

* cited by examiner

*Primary Examiner*—Richard L. Raymond
*Assistant Examiner*—Al Kahsay Habte
(74) *Attorney, Agent, or Firm*—Arthur Mann; William Lee

(57) ABSTRACT

A process is provided for producing a compound having the formula:

(1.0)

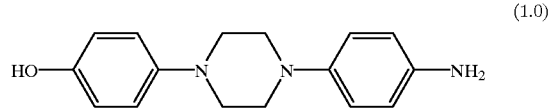

by:
(a) reacting a compound having the formula (2.0)

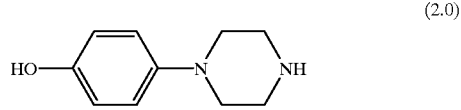

with a compound having the formula (3.0)

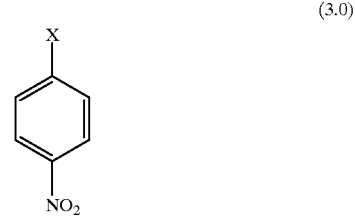

in the presence of an organic base selected from the group consisting of: triethylamine; N,N-diisopropylethylamine; 1,8-diazabicyclo[5.4.0]undec-7-ene(1,5-5); 1,5-diazabicyclo[4.3.0]non-5-ene; or 1,4-diazabicyclo[2.2.2]octane to form a compound having the formula (4.0)

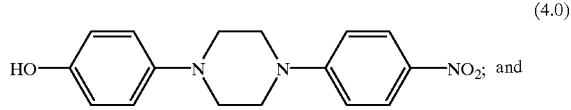

(b) reducing the compound of formula (4.0) to form the compound of formula (1.0), wherein X is Cl, Br, I or F.

10 Claims, No Drawings

PROCESS FOR PREPARING N-(4-HYDROXYPHENYL)-N'-(4'-AMINOPHENYL)-PIPERAZINE

This application claims the benefit of U.S. Provisional Application No. 60/164,296 filed Nov. 8, 1999.

The present invention provides a process for preparing N-(4-hydroxyphenyl)-N'-(4'-aminophenyl)-piperazine.

BACKGROUND OF THE INVENTION

N-(4-hydroxyphenyl)-N'-(4'-aminophenyl)-piperazine is an intermediate useful for preparing triazolones having activity as antifungals. U.S. Pat. No. 5,625,064, for example, discloses the use of this compound to prepare the triazolones described therein. Published European Patent Application No. 0 331 232 discloses a process for N-arylating a piperazine of formula (III) to produce a di-aryl piperazine of formula (I):

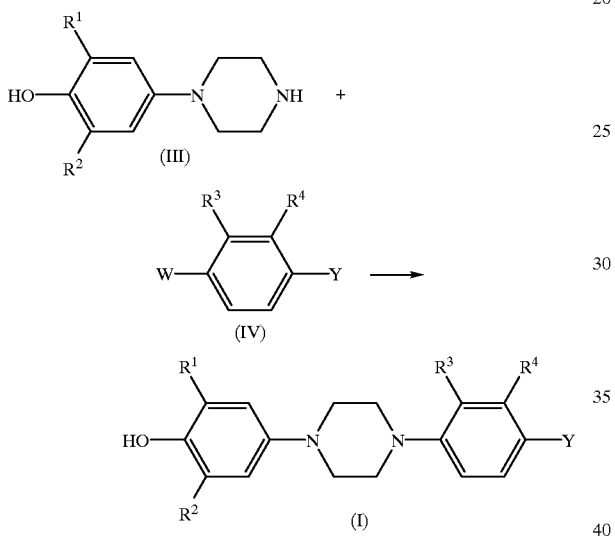

wherein $R^1$ and $R^2$ are each independently hydrogen, $C_1$–$C_6$ alkyl, or halo; $R^3$ and $R^4$ are each independently hydrogen, halo, amino, nitro or trifluoromethyl; Y is hydrogen, nitro, amino, mono- or di($C_1$–$C_6$ alkyl) amino, $C_1$–$C_6$ alkylcarbonylamino, $C_1$–$C_6$ alkyl, $C_1$–$C_6$ alkylcarbonyl, hydroxy, halo, mono- or di($C_1$–$C_6$ alkyl) aminosulfonyl, or a heterocyclic radical; and W is halo, preferably fluoro or chloro. It also discloses that the compounds of formula (I) having a nitro substituent can be converted into the corresponding amines by catalytic hydrogenation. It further discloses that the N-arylation may be carried out at an elevated temperature in an appropriate solvent in the presence of an appropriate base such as, for example, an alkali metal hydride or carbonate. However, the reported yield for the N-arylation step is poor (see Example 17) and the product produced in this step has to be purified by extraction and salt formation, making this process unsuitable for large scale production.

The present invention solves this problem by providing an efficient, high-yielding N-arylation step employing an organic base which is suitable for large scale production.

SUMMARY OF THE INVENTION

A process is provided for producing a compound having the formula:

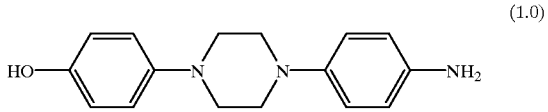

comprising:

(a) reacting a compound having the formula

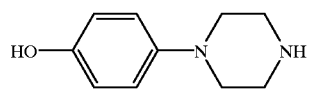

with a compound having the formula

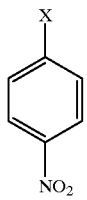

in the presence of an organic base selected from the group consisting of: triethylamine; N,N-diisopropylethylamine; 1,8-diazabicyclo[5.4.0]undec-7-ene (1,5-5); 1,5-diazabicyclo[4.3.0]non-5-ene; or 1,4-diazabicyclo[2.2.2]octane to form a compound having the formula

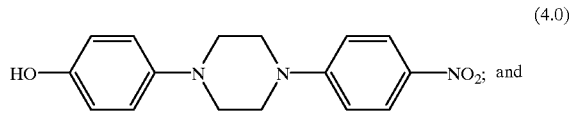

(b) reducing the compound of formula (4.0) to form the compound of formula (1.0), wherein X is Cl, Br, I or F.

DETAILED DESCRIPTION OF THE INVENTION

X is preferably Cl or F, most preferably Cl.

The organic base is preferably triethylamine or N,N-diisopropylethylamine (Hünig's base).

Certain solvents and reagents are referred to herein by the following abbreviations: N,N-diisopropylethylamine (Hünig's base); 1,8-diazabicyclo[5.4.0]undec-7-ene (1,5-5) (DBU); ; 1,5-diazabicyclo[4.3.0]non-5-ene (DBN); 1,4-diazabicyclo[2.2.2]octane (DABCO); dimethyl sulfoxide (DMSO); N,N-dimethylformamide (DMF); N-methylpyrrolidone (NMP); and dimethyltetrahydropyrimidinone (DMPU).

Compounds (2.0) and (3.0) are commercially available, or may be prepared by methods known to those skilled in the art.

Step (a) is preferably carried out at a temperature of 50° C. to 140° C., more preferably 100° C. to 130° C., most preferably 120° C. to 125° C. Step (a) is preferably carried out in an organic solvent, more preferably an aprotic organic solvent. Examples of solvents that may be used include, but are not limited to alcohols, nitrobenzene, DMSO, DMF, NMP, and DMPU. DMSO, NMP and DMPU are particularly preferred. Preferably, the amount of the para-halo-nitrobenzene compound of formula (3.0) used in step (a) is 1 to 2 equivalents, more preferably 1 to 1.5 equivalents, most preferably 1.3 to 1.4 equivalents. Preferably, the amount of organic base used in step (a) is 1 to 3 equivalents, more preferably 1 to 2 equivalents, most preferably 1.2 to 1.5 equivalents.

The compound of formula (4.0) produced in step (a) is preferably recovered by precipitation, preferably induced by the addition of isopropanol or water. Isopropanol is particularly preferred, because it produces large crystals and excess para-halo-nitrobenzene stays in solution.

In step (b), the nitro-substituted compound of formula (4.0) is reduced to form the corresponding amine of formula (1.0). The reduction is preferably carried out by means of a catalytic hydrogenation or a catalytic hydrogen transfer reduction. Examples of catalysts that may be used for the catalytic hydrogenation include, but are not limited to, Pd, Ni and Pt. An example of a hydrogen transfer agent that can be used in the catalytic hydrogen transfer reduction includes, but is not limited to sodium phosphinite monohydrate with palladium on carbon ($NaH_2PO_2.H_2O/Pd/C$).

The catalytic hydrogenation is preferably carried out at a pressure of 1–5 atm and at a temperature of 20° C. to 50° C., more preferably 20° C. to 30° C. Preferably, the catalytic hydrogenation is carried out in an organic solvent, more preferably, a protic organic solvent. Examples of solvents that may be used for the catalytic hydrogenation include, but are not limited to alcohols, such as methanol or ethanol; ethers such as THF; DMF; and NMP.

The catalytic hydrogen transfer reduction is preferably carried out at a temperature of 20° C. to 110° C., more preferably 70° C. to 75° C. The catalytic hydrogen transfer reduction is preferably carried out in an organic solvent, more preferably a protic organic solvent. Examples of solvents that may be used for the catalytic hydrogen transfer reduction include, but are not limited to methoxyethanol, n-butanol, DMF, and NMP.

Those skilled in the art will appreciate that unless stated otherwise, the compounds produced in the various process steps can, if desired, be separated from their reaction mixtures, and isolated and purified by techniques well known in the art. For example, separation can be accomplished by precipitation, chromatography, (e.g., column), phase separation (extraction) and distillation. The desired product can then be dried and purified by recrystallization.

The following examples illustrate the foregoing invention, although such examples should not be construed as limiting the scope of the invention. Alternative reagents and analagous processes within the scope of the invention will be apparent to those skilled in the art.

EXAMPLE 1

Part A

N-(4-Hydroxyphenyl)-N'-(4'-nitrophenyl)-piperazine

Under nitrogen, 420 g (2.36 mol) N-(4-Hydroxyphenyl)-piperazine, 520.6 g (3.30 mol) 1-chloro-4-nitrobenzene and 457.5 g (3.54 mol) N,N-Diisopropylethylamine (Hünig's Base) are suspended in 1260 ml N-Methylpyrrolidone and heated to 120°–125° C. The clear solution is stirred at 120°–125° C. and the reaction is followed by HPLC. After complete reaction (5–7 hours) the solution is cooled to 75°–80° C. and 6.3 liters of isopropanol are added over a period of about 30 minutes to the reaction mixture while keeping the temperature at 75°–80° C. (slight heating is necessary). Towards the end of the addition the product starts to precipitate (yellow crystals). The suspension is cooled to 20°–25° C. and stirred overnight at this temperature. Afterwards the suspension is cooled to −10° to −5° C. and stirred for 30 minutes. The product is filtered off, washed with 1.7 liters isopropanol, followed by 5×840 ml warm (35°–40° C.) water. The product is dried under vacuum at 50° C. (slight stream of nitrogen) to constant weight.

Yield: 96%

Assay (HPLC): 93% pure vs. standard

Part B

N-(4-Hydroxyphenyl)-N'-(4'-aminophenyl)-piperazine

Under nitrogen, 430 g (1.34 mol) N-(4-Hydroxyphenyl)-N'-(4'-nitrophenyl)-piperazine are suspended in 2.8 liters methoxyethanol at 20°–25° C. After the addition of 52 g palladium ((5% on charcoal, 50% water wet) (Degussa Typ E1049)) the suspension is degassed (3 times) and heated to 70°–75° C. A solution of 497 g sodium hypophosphite monohydrate in 1.12 liters water is slowly added over 2 –2.5 hours at 70°–75° C. (After addition of about 10 ml the evolution of hydrogenation starts and the temperature has to be kept at 75°–80° C.; towards the end of the addition external heating is needed). After complete addition, the reaction mixture is stirred at 70°–75° C. and the reaction is followed by TLC (silicagel, n-hexane/ethylacetate ½). After complete conversion (30 –45 minutes, color turns from brown-yellow to grey) the suspension is cooled to 25°–30° C. and diluted with 2.4 liters water. The pH is adjusted to $\leq 2$ by the addition of about 400 ml concentrated HCl (about 10 minutes) at 25° to 30° C. and stirred at this temperature for about 15 minutes. The catalyst is filtered off and washed with 600 ml water.

The combined filtrates are warmed to 35° to 40° C. and the pH is adjusted to 7.1±1 at 35° to 40° C. by the addition of about 760 ml concentrated sodium hydroxide (slightly exothermic). The resulting suspension is cooled to 20°–25° C. and stirred at that temperature for 30 minutes. The product is filtered off under nitrogen (about 40 minutes) and washed twice with 1.6 liters water, followed by 400 ml water/methanol (1:1) and 800 ml methanol. The product is dried under vacuum at 50° C. (slight stream of nitrogen) to constant weight.

Yield: 317 g (88%)

Assay (HPLC): 99.7% pure by area

EXAMPLE 2

Using substantially the same procedure as in Example 1, substitute triethylamine for Hünig's base.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

We claim:

1. A process is provided for producing a compound having the formula:

comprising:

(a) reacting a compound having the formula

(1.0)

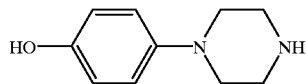
(2.0)

with a compound having the formula

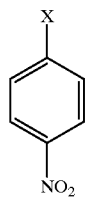
(3.0)

wherein X is Cl, Br, I or F, in the presence of an organic base selected from the group consisting of: triethylamine; N,N-diisopropylethylamine; 1,8-diazabicyclo[5.4.0]undec-7-ene (1,5-5); 1,5-diazabicyclo[4.3.0]non-5-ene; and 1,4-diazabicyclo[2.2.2]octane to form a compound having the formula

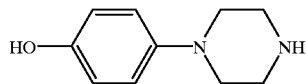
(4.0)

(b) reducing the compound of formula (4.0) to form the compound of formula (1.0).

2. The process of claim 1, wherein the organic base is triethylamine or N,N-diisopropylethylamine.

3. The process of claim 2, wherein the organic base is triethylamine.

4. The process of claim 3, wherein X is Cl or F.

5. The process of claim 3, wherein X is F.

6. The process of claim 3, wherein X is Cl.

7. The process of claim 2, wherein the organic base is N,N-diisopropylethylamine.

8. The process of claim 7, wherein X is Cl or F.

9. The process of claim 8, wherein X is F.

10. The process of claim 7, wherein X is Cl.

* * * * *